United States Patent
Sayama et al.

(10) Patent No.: US 6,756,522 B2
(45) Date of Patent: Jun. 29, 2004

(54) DISPOSABLE DIAPER

(75) Inventors: Yasushi Sayama, Kagawa-ken (JP);
Hironao Minato, Kagawa-ken (JP);
Naomi Suzuki, Kagawa-ken (JP);
Rumiko Shiraishi, Kagawa-ken (JP);
Yasushi Inoue, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 224 days.

(21) Appl. No.: 09/938,964

(22) Filed: Aug. 24, 2001

(65) Prior Publication Data

US 2002/0026171 A1 Feb. 28, 2002

(30) Foreign Application Priority Data

Aug. 24, 2000 (JP) .................................... 2000-297574

(51) Int. Cl.[7] .................................................. A61F 13/15
(52) U.S. Cl. ..................................... 604/383; 604/385.3
(58) Field of Search ................... 604/383, 385.24–385.3, 604/394

(56) References Cited

U.S. PATENT DOCUMENTS

| | | | | |
|---|---|---|---|---|
| 4,036,233 A | * | 7/1977 | Kozak | ..................... 604/370 |
| 4,710,189 A | * | 12/1987 | Lash | ..................... 604/385 |
| 4,731,066 A | | 3/1988 | Korpman | |
| 5,389,095 A | * | 2/1995 | Suzuki et al. | .......... 604/385.22 |
| 5,873,868 A | * | 2/1999 | Nakahata | ..................... 604/383 |
| 6,039,906 A | | 3/2000 | Sageser et al. | |
| 6,262,331 B1 | * | 7/2001 | Nakahata et al. | ........... 604/383 |

FOREIGN PATENT DOCUMENTS

JP        6-9620        2/1994

OTHER PUBLICATIONS

Copy of European Search Report dated Nov. 19, 2001.

* cited by examiner

Primary Examiner—John J. Calvert
Assistant Examiner—Catharine L Anderson
(74) Attorney, Agent, or Firm—Butzel Long

(57) ABSTRACT

A disposable diaper that includes a front waist region, a rear waist region, and a crotch region extending therebetween. An end portion of the rear waist region is provided with an elastic member associated with a waist-opening. The diaper has transversely opposite side edges and upper and lower edges. A plurality of slits extend through the diaper in its thickness direction and in a longitudinal direction so as to be spaced one from another by a predetermined dimension in a waist-surrounding direction between the side edges. The slits are also spaced one from another by a predetermined dimension in the longitudinal direction between a vicinity of the upper edge and a vicinity of the lower edge.

4 Claims, 5 Drawing Sheets

DISPOSABLE DIAPER

BACKGROUND OF THE INVENTION

This invention relates to a disposable wearing article adapted to absorb and to hold excretion discharged thereon.

Japanese Utility Model Application Publication No. 1994-9620A describes an open-type disposable diaper comprising a liquid-pervious topsheet, a liquid-impervious backsheet and a liquid-absorbent core disposed between these two sheets wherein a pair of flaps extending outward from transversely opposite side edges of the core are formed with a plurality of slits extending in a longitudinal direction. These slits are formed in the flaps extending in front and rear waist regions so that they are spaced one from another by a predetermined dimension in the longitudinal direction and spaced one from another by a predetermined dimension in a waist-surrounding direction. The slits are widened in the waist-surrounding direction as the flaps are pulled in the waist-surrounding direction and thereupon a plurality of openings are defined in the flaps. With this diaper of prior art put on a wearer's body, dampness generated within the diaper can be relieved out through the openings and thereby undesirable stuffiness can be avoided.

However, the diaper disclosed in the Publication is not formed with the slits in the vicinity of longitudinally opposite end portions of the diaper in the front and rear waist regions. Consequently, it is impossible for the diaper to avoid stuffiness possibly occurring in the longitudinally opposite end portions tightly placed against the wearer's skin. In addition, the flaps extending outward from the front waist region are placed upon the respective flaps extending outward from the rear waist region and the openings may often be closed by the flaps placed one upon another in this manner. In other words, it is apprehended that the openings do not function as vent holes.

SUMMARY OF THE INVENTION

It is an object of this invention to provide a disposable diaper designed so that the openings defined as the diaper is put on the wearer's body may be kept open and thereby stuffiness possibly occurring particularly in the vicinity of the longitudinally opposite end portions of the diaper.

According to this invention, there is provided a disposable diaper comprising a liquid-pervious topsheet, a liquid-impervious backsheet and a liquid-absorbent core disposed between these sheets so as to define a front waist region, a rear waist region and a crotch region extending between these waist regions, and an elastic member which is stretchable in a waist-surrounding direction being bonded under tension to at least one of longitudinally opposite end portions of the diaper in the front and rear waist regions.

According to this invention the elastic member associated with the waist-opening has transversely opposite ends extending in the longitudinal direction and upper and lower edges extending in the waist-surrounding direction, and a plurality of slits extending through the diaper in a thickness direction thereof and extending in the longitudinal direction are arranged to be spaced one from another by a predetermined dimension in the waist-surrounding direction between the transversely opposite ends of the elastic member associated with the waist-opening and spaced one from another by a predetermined dimension in the longitudinal direction between the vicinity of the upper edge and the vicinity of the lower edge of the elastic member associated with the waist-opening.

According to one embodiment of this invention, the slits are formed in the middle zone of the elastic member associated with the waist-opening as viewed in the waist-surrounding direction.

According to another embodiment of this invention, each of the slits is dimensioned in the longitudinal direction so as to be progressively reduced from the array of the slits defined in the vicinity of the upper edge to the array of the slits defined in the vicinity of the lower edge of the elastic member associated with the waist-opening.

DETAILED DESCRIPTION OF THE REFERENCED EMBODIMENTS

Details of a disposable diaper according to this invention will be more fully understood from the description of an open-type disposable diaper and a briefs-type disposable diaper as embodiments of this invention given hereunder with reference to the accompanying drawings.

Figure 1:
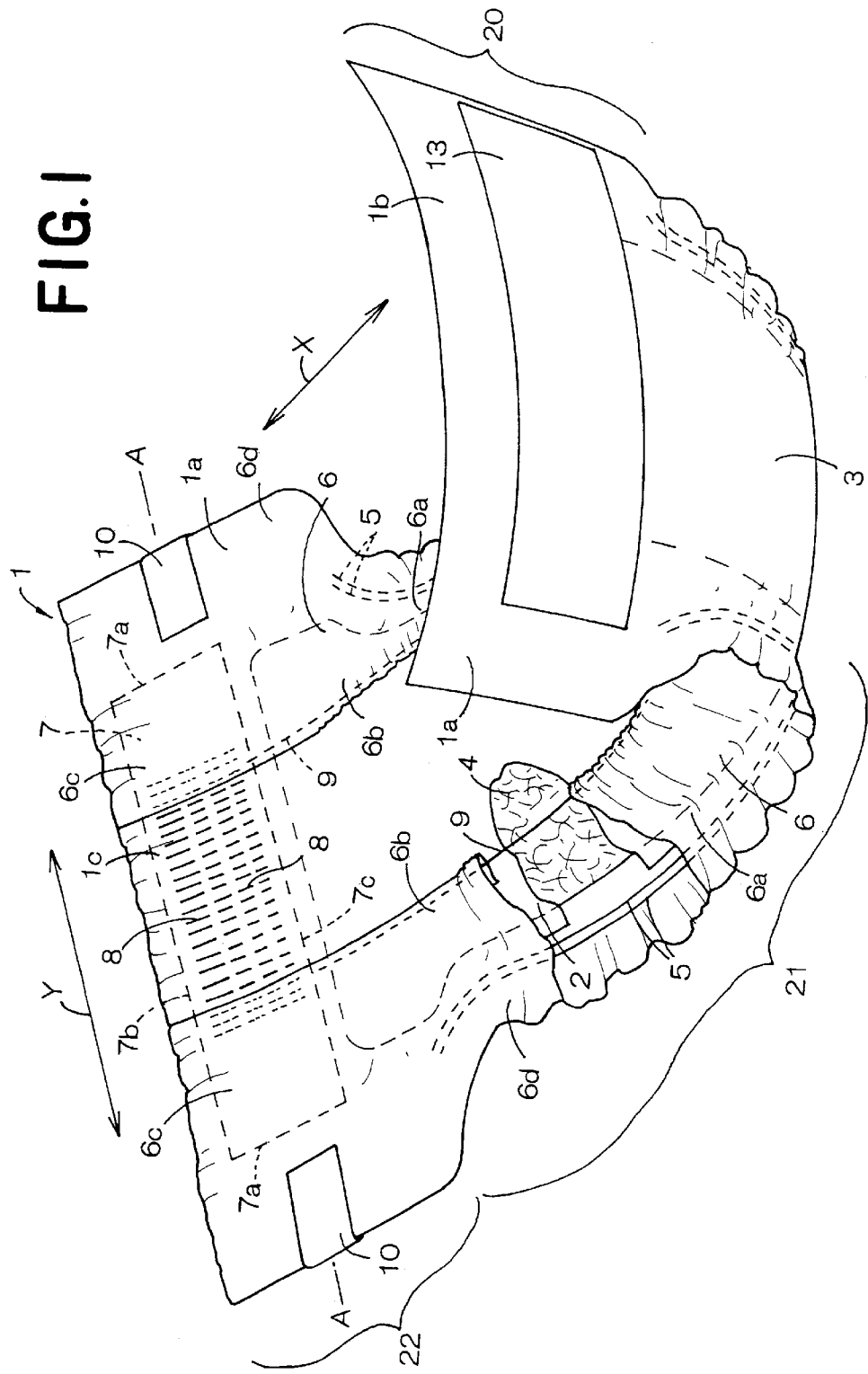
FIG. 1 is a perspective view showing an open-type diaper as partially broken away.
Figure 2:
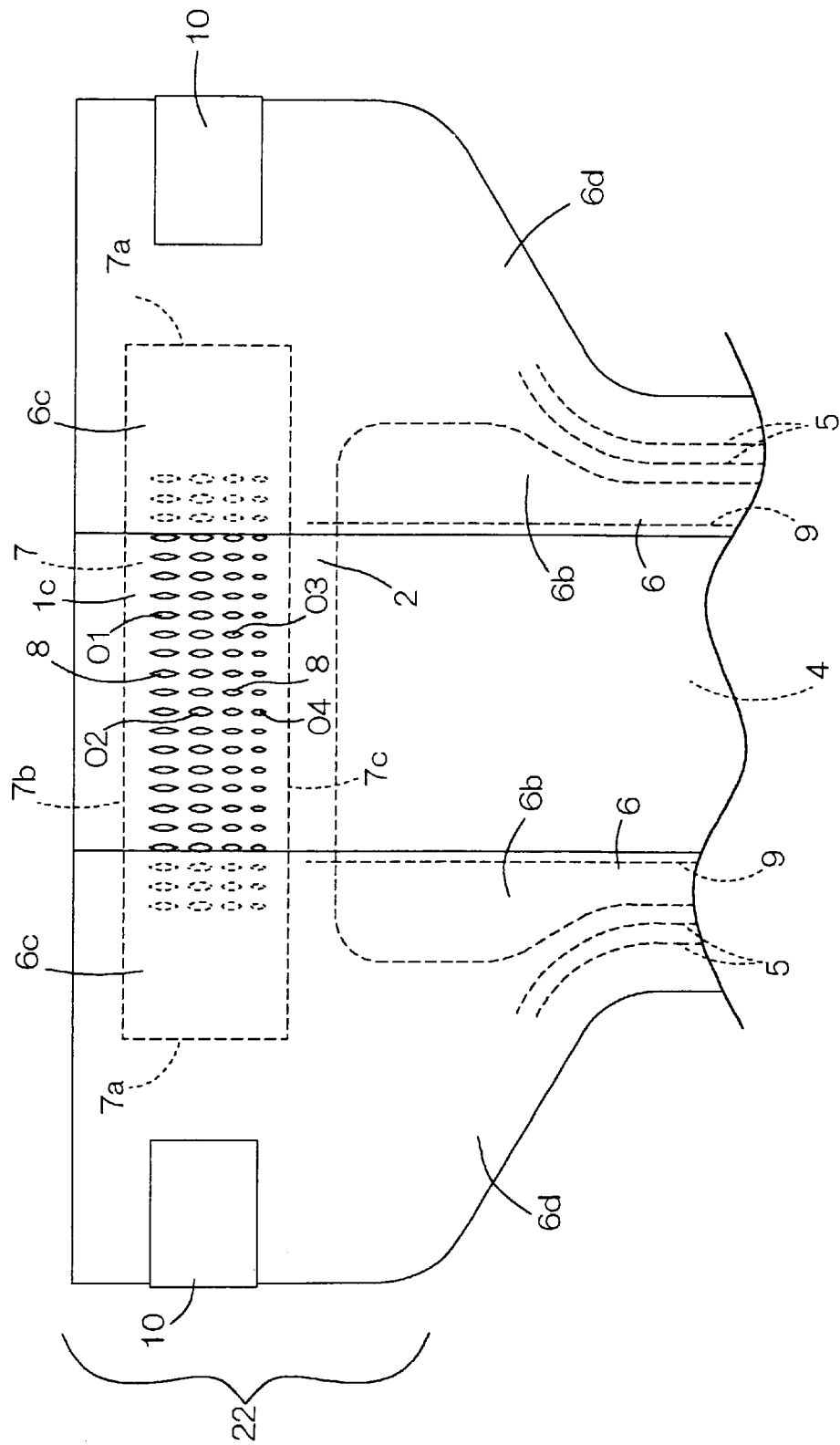
FIG. 2 is a plan view showing the rear waist region of the diaper.
Figure 3:
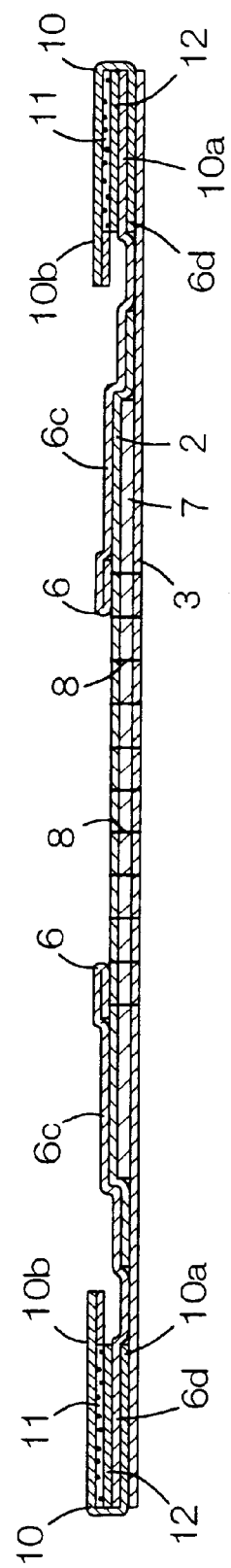
FIG. 3 is a sectional view taken along a line A—A in FIG. 1.

FIG. 1 is a perspective view showing an open-type diaper as partially broken away, FIG. 2 is a plan view showing a rear waist region of the diaper and FIG. 3 is a sectional view taken along a line A—A in FIG. 1. Referring to FIG. 1, a longitudinal direction is indicated by an arrow X and a transverse direction is indicated by an arrow Y. FIG. 2 illustrates slits 8 widened in the transverse direction to define a plurality of openings O1~O4 each arranged along one end portion 1c of longitudinally opposite ends 1b of the diaper 1. Surfaces of various members such as top- and backsheets 2,3 and leak-barrier sheets 6 facing a core 4 are referred to herein as inner surfaces thereof and surfaces of these members not facing the core 4 are referred to herein as outer surfaces thereof.

The diaper 1 basically comprises the liquid-pervious topsheet 2, the liquid-impervious backsheet 3 and the liquid-absorbent core 4 disposed between these top- and backsheets 2, 3 and entirely covered with and bonded to a liquid-dispersive sheet such as tissue paper (not shown). The core 4 is, in turn, bonded to the inner surface of the topsheet 2 and/or the backsheet 3 with the liquid-dispersive sheet therebetween.

The diaper 1 is defined, in the longitudinal direction, of a front waist region 20, a rear waist region 22 and a crotch region 21 extending between the front and rear waist regions 20, 22. The diaper 1 is contoured by transversely opposite side edge portions 1a extending in parallel to each other in the longitudinal direction so as to define circular arcs curving inward transversely of the diaper 1 and the longitudinally opposite end portions 1b, 1c extending in parallel to each other in the transverse direction.

The crotch region 21 is provided along the transversely opposite side edge portions 1a with elastic members 5 extending in the longitudinal direction and each comprising a plurality of elastic elements. These elastic members 5 are attached under tension to the diaper 1 so as to be associated with respective leg-openings. The transversely opposite side edge portions 1a are provided a pair of leak-barrier sheets 6 extending in the longitudinal direction.

The end portion 1c in the rear waist region 22 is provided with a ribbon-like elastic member 7 associated with a waist-opening, which is stretchable in the transverse direction and attached under tension to the end portion 1c. In the end portion 1c, a plurality of slits 8 extending through the top- and backsheets 2, 3 and the elastic member 7 associated with the waist-opening are arranged in the longitudinal direction.

The elastic member 7 associated with the waist-opening is disposed between the top- and backsheets 2, 3 and bonded to the inner surface of at least one of these sheets 2, 3. The elastic member 7 associated with the waist-opening has transversely opposite side edges 7a extending in parallel to each other in the longitudinal direction and upper and lower edges 7b, 7c extending in parallel to each other in the transverse direction.

The slits 8 are formed in a transversely middle zone of the elastic member 7 associated with the waist-opening and arranged to be spaced one from another by a predetermined dimension between the transversely opposite side edges 7a of the elastic member 7 associated with the waist-opening. Also between the upper and lower edges 7b, 7c of the elastic member 7 associated with the waist-opening, the slits 8 are arranged to be spaced one from another by a predetermined dimension in the longitudinal direction. Each of the slits 8 is dimensioned in the longitudinal direction so that this dimension is progressively reduced from the array of the slits 8 defined in the vicinity of the upper edge 7b of the elastic member 7 associated with the waist-opening to the array of the slits 8 defined in the vicinity of the lower edge 7c of the elastic member associated with the waist-opening.

Each of the leak-barrier sheets 6 has a fixed side edge portion 6a and a free side edge portion 6b both extending in the longitudinal direction and longitudinally opposite end portions 6c collapsed inward in the transverse direction of the diaper 1 to be placed upon the topsheet 2. The leak-barrier sheet 6 further includes a laterally extended portion 6d extending outward from the fixed side edge portion 6a in the transverse direction. The fixed side edge portions 6a and the longitudinally opposite end portions 6c are bonded to the outer surface of the topsheet 2. An elastically stretchable members 9 extending in the longitudinal direction are bonded under tension to the respective free side edge portions 6b. The elastic members 9 are covered with parts of the respective free side edge portion 6b.

A tape fasteners 10 are respectively attached to the rear waist region 22 and extend inward from the transversely opposite side edge portions 1a in the transverse direction. The tape fasteners 10 have their proximal end portions 10a disposed between the backsheet 3 and the laterally extended portions 6d of the leak-barrier sheets 6 and bonded to the inner surfaces of these sheets 3, 6. The tape fasteners 10 have their free side edge portions 10b coated with pressure-sensitive adhesive 11 by means of which these free side edge portions 10b are temporarily bonded to sheets of plastic film 12 which are, in turn, bonded to the laterally extended portions 6d of the respective leak-barrier sheets 6. In the front waist region 20, a target tape strip 13 made of plastic film is attached to the outer surface of the backsheet 3. The target tape strip 13 defines a landing zone of the tape fasteners 10.

Along the transversely opposite side edge portions 1a of the diaper 1, the topsheet 2 extends outward slightly beyond the transversely opposite side edges of the core 4. The backsheet 3 and the laterally extended portions 6d of the respective leak-barrier sheets 6 extend further outward beyond the transversely opposite side edges of the topsheet 2. Along the transversely opposite side edge portions 1a of the diaper 1, the portions of the top- and backsheets 2, 3 and laterally extended portions 6d of the respective leak-barrier sheets 6 are put flat and bonded together. Each of the elastic members 5 associated with the leg-openings is disposed between the backsheet 3 and the laterally extended portion 6d of the leak-barrier sheet 6 and bonded to the inner surface of at least one of these sheets 3, 6. Along the longitudinally opposite end portions 1b and 1c of the diaper 1, the portions of the top- and backsheets 2, 3 and the leak-barrier sheets 6 extending outward in the longitudinal direction beyond longitudinally opposite ends of the core 4 are put flat and bonded together.

Referring to FIG. 1, a plurality of gathers are fanned along the transversely opposite side edge portions 1a as well as the longitudinally opposite end portions 1c of the diaper 1 and along the free side edge portions 6b of the respective leak-baffler sheets 6 as the elastic members 5, 7, 9 contract. At the same time, the diaper 1 is curved in the longitudinal direction with the topsheet 2 inside and the free side edge portions 6b of the respective leak-barrier sheets 6 are erected upward as viewed in FIG. 1 under the contractile force of the elastic members 9. As will be apparent from FIG. 2, a total area of each ray of the openings O1, O2, O3, O4 defined in the end portion 1c of the rear waist region 22 is progressively reduced from the ray of openings O1 defined in the vicinity of the upper edge 7b toward the array of openings O4 defined in the vicinity of the lower edge 7c of the elastic member 7 associated with the waist-opening.

An alternative arrangement is also possible in which the slits 8 arranged in the vicinity of the upper edge 7b of the elastic member 7 associated with the waist-opening extend in the longitudinal direction across this upper edge 7b so as to extend slightly beyond this edge 7b and the slits 8 arranged in the vicinity of the lower edge 7c of the elastic member 7 associated with the waist-opening extend in the longitudinal direction across this lower edge 7c so as to extend slightly beyond this edge 7c. In this case, the portions of the respective slits 8 extending beyond the upper and lower edges 7b, 7c should extend through the top- and backsheets 2, 3.

Figure 4:
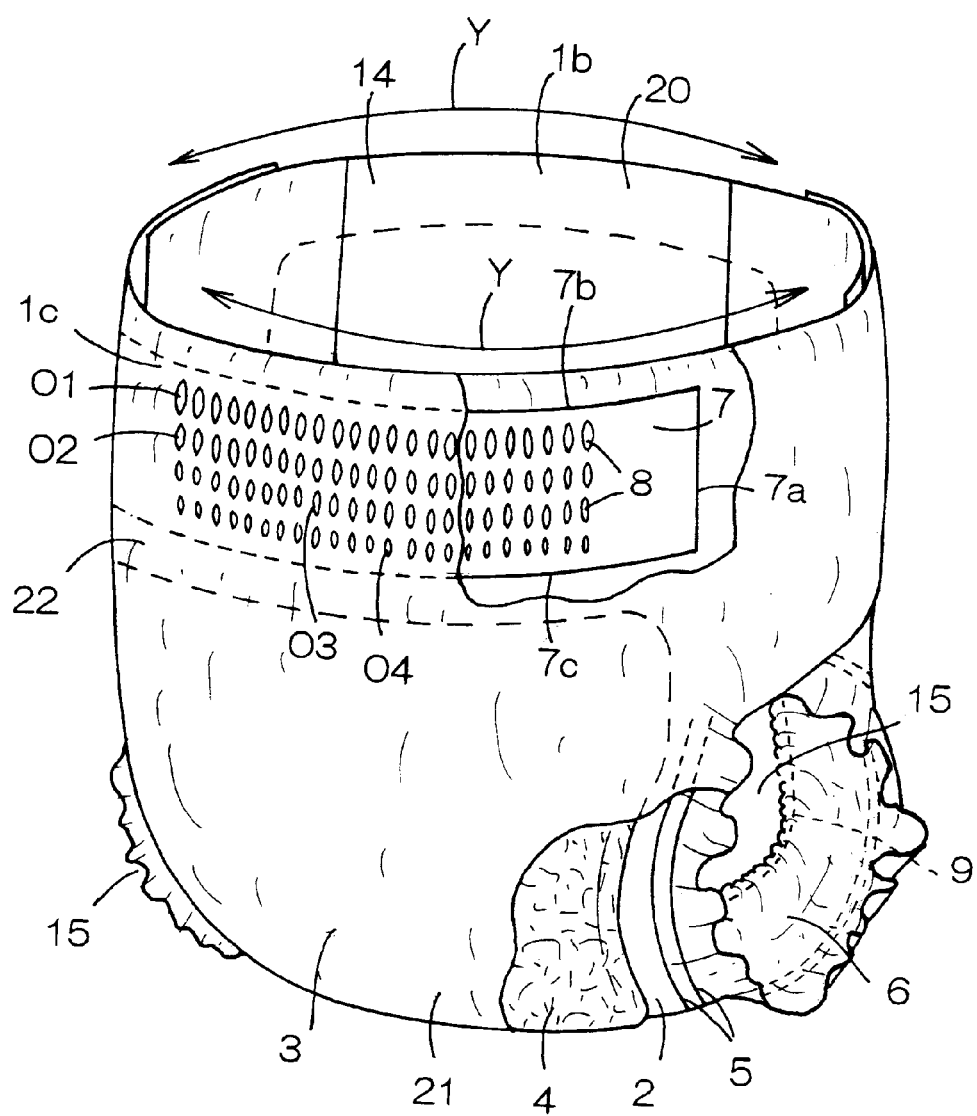
FIG. 4 is a perspective view showing the diaper as put on a wearer's body with the front and rear waist regions connected to each other.

FIG. 4 is a perspective view showing the diaper 1 with the front and rear waist regions 20, 22 connected together as put on a wearer's body, in which a waist-surrounding direction is indicated by an arrow Y. To put the diaper 1 on the wearer s body, the transversely opposite side edge portions 1a of the rear waist region 22 are overlapped upon the outer side of the front waist region 20 along its transversely opposite side edge portions 1a and then the free end portions 10b of the respective tape fasteners 10 are anchored on the target tape strip 13 by means of pressure-sensitive adhesive 11. The diaper 1 defines a waist-opening 14 and a pair of leg-openings 15 as the front and rear waist regions 20, 22 are connected together in this manner.

In referring to FIG. 4, the rear waist region 22 is pulled in the waist-surrounding direction so that the transversely opposite side edges 1a thereof are spaced apart from each other. The elastic member 7 associated with the waist-opening is correspondingly stretched in the waist-surrounding direction and the slits 8 are widened so define a plurality of openings O1~O4 which are longitudinally larger. The end portion 1c of the diaper 1 in the rear waist region 22 is tightly held against the wearer's skin under the contractile force of the elastic member 7 associated with the waist-opening and the diaper 1 would be liable to undesirable stuffiness. However, the diaper 1 is provided along the longitudinal opposite end portions 1c with a plurality of openings O1~O4 extending through the top- and backsheets 2, 3 as well as the elastic member 7 associated with the waist-opening. Dampness generated within the diaper 1 can be relieved out through these openings defined in the vicinity of the end portion 1c and thereby stuffiness possibly occurring in this end portion 1c can be effectively avoided.

The total area of the arrays of openings O3, O4 defined in the vicinity of the lower edge 7c is smaller than the total area of the arrays of openings O1, O2 defined in the vicinity of the upper edge 7b of the elastic member 7 associated with the waist-opening. Such arrangement minimizes an anxiety that excretion discharged on the diaper 1 might leak through the arrays of openings O3, O4 defined in the vicinity of the lower edge 7c and prevents an amount of the excretion permeating the end portion 1c of the diaper 1 from leaking out from the diaper 1 through the openings O3, O4. The elastic member 7 associated with the waist-opening contracts again and the openings O1~O4 are closed again as the tape fasteners 11 are disengaged from the target tape strip 13.

Figure 5:
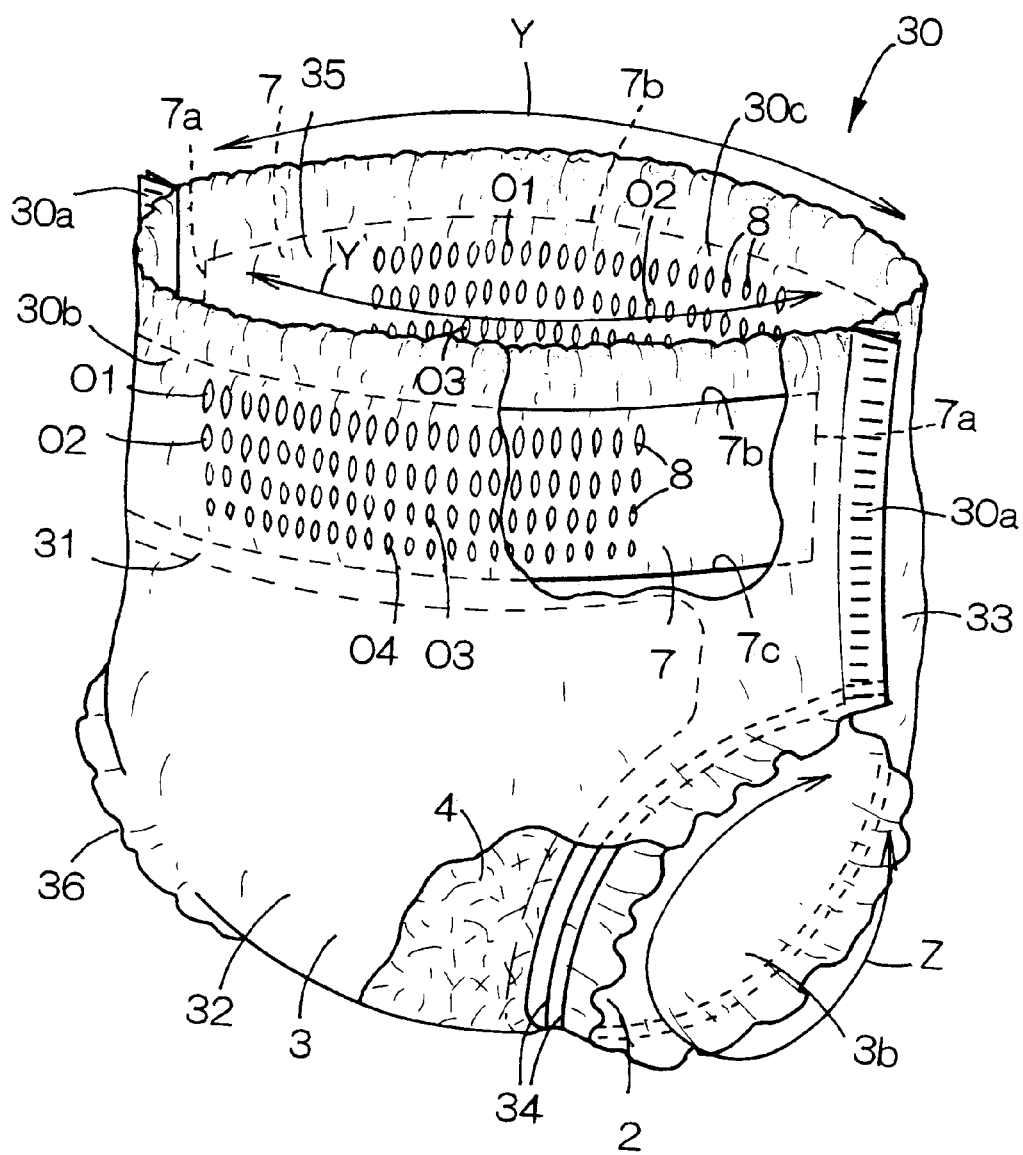
FIG. 5 is a perspective view showing the pants-type diaper as put on a wearer's body and as partially broken away.

FIG. 5 is a perspective view showing a pants-type diaper 30 as put on a wearer's body and as partially broken away, in which a waist-surrounding direction is indicated by an arrow Y and a thigh-surrounding direction is indicated by an arrow Z. In referring to FIG. 5, the slits 8 are widened in the waist-surrounding direction and a plurality of openings O1~O4 are defined along front and rear peripheral edges 30b, 30c of the waist-opening 35. Similarly to the diaper 1 of FIG. 1, the diaper 30 basically comprises the liquid-pervious topsheet 2, the liquid-impervious backsheet 3 and the liquid-absorbent core 4 disposed between these sheets 2, 3 and entirely covered with and bonded to tissue paper (not shown).

The diaper 30 is basically composed of front and rear waist regions 31, 33 opposed to each other and a crotch region 32 extending between the front and rear waist regions 31, 33 so that the front and rear waist regions 31, 33 have their transversely opposite side edge portions 30a put flat and bonded together to define a waist-opening 35 and a pair of leg-openings 36.

Elastic members 34 each comprising a plurality of elastic elements and being stretchable in the thigh-surrounding direction are bonded under tension to respective peripheral edge portions of the respective leg-openings 36. These elastic members 34 associated with the leg-openings 36 are disposed between the top- and backsheets 2, 3 and bonded to the inner surface of at least one of these sheets 2, 3.

The front and rear peripheral edge portions 30b, 30c of the waist-opening 35 are respectively provided with a pair of ribbon-like elastic members 7 being stretchable in the waist-surrounding direction and bonded under tension thereof so as to be associated with the waist-opening 35. In the respective peripheral edge portions 30b, 30c, a plurality of slits 8 extend in the longitudinal direction and, in the thickness direction of the diaper 30, these slits 8 extend through the top- and backsheets 2, 3 as well as the elastic members 7 associated with the waist-opening.

The elastic members 7 associated with the waist-opening are disposed between the top- and backsheets 2, 3 and bonded to the inner surface of at least one of these sheets 2, 3. Each of the elastic member 7 associated with the waist-opening has transversely opposite side edges 7a extending in parallel to each other in the longitudinal direction and upper and lower edges 7b, 7c extending in parallel to each other in the transverse direction.

The slits 8 are formed in transversely middle zones of the respective elastic members 7 associated with the waist-opening and arranged to be spaced one from another by a predetermined dimension between the transversely opposite side edges 7a of respective the elastic members 7 associated with the waist-opening. Also between the upper and lower edges 7b, 7c of the respective elastic members 7 associated with the waist-opening, the slits 8 are arranged to be spaced one from another by a predetermined dimension in the longitudinal direction. Each of the slits 8 is dimensioned in the longitudinal direction so that this dimension is progressively reduced from the array of the slits 8 defined in the vicinity of the upper edges 7b to the array of the slits 8 defined in the vicinity of the lower edges 7c of the respective elastic member 7 associated with the waist-opening.

The respective elastic members 7 associated with the waist-opening are stretched in the waist-surrounding direction as the diaper 30 is put on the wearer's body, and thereupon the slits 8 are widened to define a plurality of openings O1~O4 each being longitudinally larger. The plurality of openings O1~O4 defined in the front and rear peripheral edge portions 30b, 30c and extending through the top- and backsheets 2, 3 as well as the elastic members 7 associated with the waist-opening advantageously allow dampness generated within the diaper 30 and eliminate an anxiety that undesirable stuffiness might occur in the vicinity of the front and rear peripheral edge portions 30b, 30c.

The total area of the arrays of openings O3, O4 defined in the vicinity of the lower edges 7c is smaller than the total area of the arrays of openings O1, O2 defined in the vicinity of the upper edges 7b of the respective elastic members 7 associated with the waist-opening. Such unique arrangement eliminates an anxiety that excretion discharged on the diaper 30 might leak out through the arrays of openings O3, O4 defined in the vicinity of the respective lower edges 7c.

The topsheet 2 may be formed from a liquid-pervious sheet such as a nonwoven fabric or porous plastic film, preferably from a liquid-pervious hydrophilic sheet. The backsheet 3 may be formed from a hydrophobic nonwoven fabric, liquid-impervious plastic film or a laminated sheet of hydrophobic nonwoven fabric and plastic film, preferably from a breathable but liquid-impervious sheet. It is also possible to form the backsheet 3 using a composite nonwoven fabric consisting of a melt blown nonwoven fabric having a high water-resistance and two layers of a spun bond nonwoven fabric having high strength and flexibility sandwiching the melt blown nonwoven fabric.

The nonwoven fabric may be selected from a group including spun lace-, needle punch-, melt blown-, thermal bond-, spun bond-, chemical bond- and air through-nonwoven fabrics. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

Each of the elastic members 7 associated with the waist-opening may be formed from foamed materials such as soft urethane foam, synthetic rubber foam of styrene foam, or non-foamed elastomer film of natural or synthetic rubber.

The core 4 is a mixture of fluff pulp, high absorption polymer particles and thermoplastic synthetic resin fiber compressed to a desired thickness. The high absorption polymer may be selected from a group including graft polymer of starch, denaturated cellulose, crosslinked water-soluble polymer and alkali metal acrylate of self-crosslinkage type.

Bonding of the top- and backsheets to each other, bonding the core 4 to the top- and backsheets 2, 3 as well as attaching of the elastic member 5, 7, 9, 34 and tape fasteners 10 may be carried out using suitable adhesive such as a hot melt adhesive agent or a technique of welding such as a sonic sealing or a heat-sealing.

The disposable diaper according to this invention has a unique arrangement of plural slits extending through the thickness direction of the diaper and extending in the longitudinal direction. These slits are arranged between the longitudinally opposite ends and between the upper and lower edges of the elastic member associated with the waist-opening so that the slits are widened in the waist-surrounding direction and a plurality of openings are defined in the vicinity of at least one of the longitudinally opposite end portions of the diaper as the diaper is put on the wearer s body. Such arrangement ensures that dampness generated within the diaper can be relieved out through the openings and stuffiness possibly occurring in the longitudinally opposite end portions of the diaper can be reliably avoided even if the end portions of the diaper are tightly placed against the wearer's body under a contractile force of the elastic member associated with the waist-opening.

With the diaper according to this invention implemented as the open-type diaper formed in the middle zone of the elastic member associated with the waist-opening as viewed in the waist-surrounding direction, it is not apprehended that the openings might be closed by the transversely opposite side edge portions of the front and rear waist regions placed one upon another as the diaper of prior art has been the case.

With the diaper having the slits dimensioned in the longitudinal direction so as to be progressively reduced from the upper edge toward the lower edge of the elastic member associated with the waist-opening, the area of each slit is also progressively reduced from the upper edge toward the lower edge of the elastic member associated with the waist-opening. Consequently, it is not apprehended that excretion discharged on the diaper and permeating the longitudinally opposite end portions of the diaper might leak out from the diaper through the openings.

What is claimed is:

1. A disposable diaper comprising:
   a liquid-pervious topsheet;
   a liquid-impervious backsheet;
   a liquid-absorbent core disposed between the liquid-pervious topsheet and the liquid-impervious backsheet;
   a front waist region;
   a rear waist region;
   a crotch region extending between said front waist and said rear waist region;
   an elastic member bonded under tension to at least one of longitudinal opposite end portions of the diaper in said front and rear waist region with said elastic member disposed between said liquid-pervious topsheet and said liquid-impervious backsheet, said elastic member being stretchable in a waist-surrounding direction;
   said elastic member having transversely opposite ends extending in a longitudinal direction of said diaper and upper and lower edges extending in said waist-surrounding direction; and
   a plurality of slits extending through said diaper in a thickness direction of said diaper and extending in said longitudinal direction, the plurality of slits being spaced one from another by a predetermined dimension in said waist-surrounding direction between said transversely opposite ends of said elastic member and spaced one from another by a predetermined dimension in said longitudinal direction between a vicinity of said upper edge and a vicinity of said lower edge of said elastic member.

2. The diaper according to claim 1, wherein said plurality of slits are formed in a middle zone of said elastic member in said waist-surrounding direction.

3. The diaper according to claim 1, wherein each of said plurality of slits comprises a plurality of rows of slits extending in the longitudinal direction, each row of slits having a longitudinal dimension that is progressively reduced in size between adjacent rows of slits from said upper edge of said elastic member to said lower edge of said elastic member.

4. The diaper according to claim 1, wherein said elastic member has a transversal length which is greater than a transversal width of the crotch region.

* * * * *